United States Patent
Khattar et al.

(10) Patent No.: US 9,669,048 B2
(45) Date of Patent: Jun. 6, 2017

(54) STABLE PHARMACEUTICAL COMPOSITION OF 5-AZA-2'-DEOXYCITIDINE

(71) Applicant: Fresenius Kabi Oncology Limited, New Delhi (IN)

(72) Inventors: Dhiraj Khattar, Gurgaon (IN); Rajesh Khanna, Gurgaon (IN); Sanjay Motwani, Gurgaon (IN); Sunny Chopra, Gurgaon (IN); Minakshi Garg, Gurgaon (IN)

(73) Assignee: Fresenius Kabi Oncology Limited, New Dehli (IN)

( * ) Notice: Subject to any disclaimer, the term of this patent is extended or adjusted under 35 U.S.C. 154(b) by 52 days.

(21) Appl. No.: 14/436,572

(22) PCT Filed: Oct. 24, 2013

(86) PCT No.: PCT/IN2013/000649
§ 371 (c)(1),
(2) Date: Apr. 17, 2015

(87) PCT Pub. No.: WO2014/064717
PCT Pub. Date: May 1, 2014

(65) Prior Publication Data
US 2016/0166593 A1   Jun. 16, 2016

(30) Foreign Application Priority Data
Oct. 25, 2012 (IN) .......................... 3284/DEL/2012

(51) Int. Cl.
| A61K 31/706 | (2006.01) |
| A61K 9/00 | (2006.01) |
| A61K 47/18 | (2017.01) |
| A61K 9/08 | (2006.01) |
| A61K 31/7068 | (2006.01) |
| A61K 47/10 | (2017.01) |
| B65B 3/00 | (2006.01) |
| B65B 7/16 | (2006.01) |

(52) U.S. Cl.
CPC .......... *A61K 31/706* (2013.01); *A61K 9/0019* (2013.01); *A61K 9/08* (2013.01); *A61K 31/7068* (2013.01); *A61K 47/10* (2013.01); *A61K 47/18* (2013.01); *B65B 3/003* (2013.01); *B65B 7/161* (2013.01)

(58) Field of Classification Search
None
See application file for complete search history.

(56) References Cited

U.S. PATENT DOCUMENTS

| 4,684,630 | A | 8/1987 | Repta et al. |
| 6,982,253 | B2 | 1/2006 | Joshi-Hangal et al. |
| 7,135,464 | B2 * | 11/2006 | Joshi-Hangal ....... A61K 9/0019 514/42 |
| 2003/0181527 | A1 * | 9/2003 | Andersson ........... A61K 9/0019 514/645 |
| 2003/0229047 | A1 | 12/2003 | Joshi-Hangal et al. |
| 2004/0186284 | A1 * | 9/2004 | Ionescu .................. C07H 1/06 536/28.3 |
| 2010/0087637 | A1 * | 4/2010 | Henschke .............. C07H 19/12 536/28.3 |
| 2012/0196823 | A1 | 8/2012 | Tutino et al. |

\* cited by examiner

*Primary Examiner* — Shaojia Anna Jiang
*Assistant Examiner* — Dale R Miller
(74) *Attorney, Agent, or Firm* — Occhiuti & Rohlicek LLP

(57) ABSTRACT

Described herein are ready to use, non-aqueous pharmaceutical compositions comprising 5-aza-2'-deoxycitidine and at least one aprotic solvent. The pharmaceutical compositions may further comprise at least one protic solvent. Also described are processes for preparing the pharmaceutical compositions and their use for the treatment of patients suffering from myelodysplastic syndromes.

15 Claims, No Drawings

STABLE PHARMACEUTICAL COMPOSITION OF 5-AZA-2'-DEOXYCITIDINE

CROSS REFERENCE TO RELATED APPLICATIONS

This application is a U.S. national stage application under 35 U.S.C. §371 of International Application No. PCT/IN2013/000649, filed on Oct. 24, 2013, which claims priority to Indian Application No. 3284/DEL/2012, filed on Oct. 25, 2012, the contents of which are hereby incorporated by reference herein in their entirety.

FIELD OF THE INVENTION

The present invention relates to stable, ready to use, non aqueous pharmaceutical compositions comprising 5-aza-2'-deoxycitidine and at least one aprotic solvent. The pharmaceutical compositions may further comprise at least one protic solvent. The pharmaceutical compositions thus prepared can be used for the treatment of patients suffering from myelodysplastic syndromes.

BACKGROUND OF THE INVENTION 5-aza-2'-deoxycitidine (Decitabine) is an analogue of the natural nucleoside 2'-deoxycytidine and is shown in Figure 1.

Figure 1: Structure of Decitabine

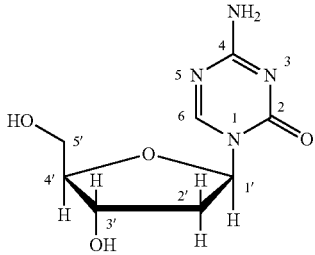

Decitabine is believed to exert its antineoplastic effects after phosphorylation and direct incorporation into DNA and inhibition of DNA methyltransferase, causing hypomethylation of DNA and cellular differentiation or apoptosis. Decitabine inhibits DNA methylation in vitro, which is achieved at concentrations that do not cause major suppression of DNA synthesis. Decitabine-induced hypomethylation in neoplastic cells may restore normal function to genes that are critical for the control of cellular differentiation and proliferation. In rapidly dividing cells, the cytotoxicity of Decitabine may also be attributed to the formation of covalent adducts between DNA methyltransferase and Decitabine incorporated into DNA. Non-proliferating cells are relatively insensitive to Decitabine.

Decitabine is commercially supplied as a sterile lyophilized powder for injection, together with a buffering salt, such as potassium dihydrogen phosphate, and a pH modifier, such as sodium hydroxide. For example, decitabine is supplied as lyophilized powder packed in 20 mL glass vials, containing 50 mg of decitabine, monobasic potassium dihydrogen phosphate, and sodium hydroxide. As per the package insert leaflet of Dacogen®, it has to be aseptically reconstituted with 10 mL of Sterile Water for Injection (USP). Upon reconstitution, each mL contains approximately 5.0 mg of Decitabine at pH 6.7-7.3. Immediately after reconstitution, the solution has to be further diluted with 0.9% Sodium Chloride Injection, 5% Dextrose Injection, or Lactated Ringer's Injection to a final drug concentration of 0.1-1.0 mg/mL. Unless used within 15 minutes after reconstitution, the diluted solution must be prepared using cold (2° C.-8° C.) infusion fluids and stored at 2° C.-8° C. (36° F.-46° F.) for up to a maximum of 7 hours until administration. It is thus apparent that Decitabine is highly unstable in aqueous media.

Decitabine is most typically administered to patients by injection, such as by a bolus I.V. injection, continuous I.V. infusion, or I.V. infusion. The length of I.V. infusion is limited by the fast decomposition of Decitabine in aqueous media.

The disadvantage of lyophilized drugs is that they have to be reconstituted, usually by injecting a diluent through the septum into the vial. The drug is then drawn up into a new syringe, the needle has to be changed before the drug is finally being injected into the patient. These multiple steps are inconvenient and bear the risk of injuries from the exposed needles. This is especially disadvantageous for cytotoxic drugs such as Decitabine.

Decitabine is known to undergo degradation by oxidation and hydrolysis. U.S. Pat. No. 6,982,253 B2 discloses a liquid pharmaceutical composition comprising Decitabine solvated in a solvent that comprises glycerin, propylene glycol, polyethylene glycol, or combinations thereof, that comprises less than 40% water. The pharmaceutical composition further comprises additional excipients e.g. diluents, an acidifying agent and a cyclodextrin. Also, the Decitabine used in the preparation of the formulation has a defined particle size distribution, such that at least 50% of the particles have a particle size of below 10 micrometers. This is achieved by micronization. However, from the data provided in table 1, it is apparent that also the pharmaceutical compositions according to U.S. Pat. No. 6,982,253 are unstable. Moreover, the pharmaceutical compositions according to U.S. Pat. No. 6,982,253 require micronization of the drug due to its limited solubility in the described solvent systems as well as the higher viscosity of the latter.

Thus there still is a need for stable ready to use pharmaceutical compositions of Decitabine overcoming the disadvantages of the prior art.

It is thus an object of the present invention to provide ready to use, non aqueous pharmaceutical compositions comprising 5-aza-2'-deoxycitidine and at least one pharmaceutically acceptable aprotic solvent. The pharmaceutical compositions may further comprise at least one pharmaceutically acceptable protic solvent.

It is another object of the present invention to control the oxygen content by the addition of antioxidants or by using an inert gas such as nitrogen.

Another object of the present invention is to provide pharmaceutical compositions that are stable under both real time and accelerated storage conditions.

Yet another object of the present invention is to avoid the micronization of Decitabine.

Yet another object of the invention is to provide more cost efficient and economical formulations of decitabine.

SUMMARY OF THE INVENTION

The present invention relates to ready to use, non aqueous pharmaceutical compositions comprising the known compound 5-aza-2'-deoxycitidine and at least one aprotic solvent. The pharmaceutical compositions may further comprise at least one protic solvent.

In one embodiment of the present invention the oxygen content is controlled by the addition of antioxidants or by using an inert gas such as nitrogen.

In another embodiment of the present invention, Decitabine is used in unmicronized form.

In yet another embodiment of the present invention the pharmaceutical compositions are stable under both real time and accelerated storage conditions.

In yet another embodiment of the invention the compositions are cost efficient and economical.

DETAILED DESCRIPTION OF THE INVENTION

In one aspect the present invention relates to ready to use, non aqueous pharmaceutical compositions comprising 5-aza-2'-deoxycitidine and at least one aprotic solvent. The pharmaceutical compositions may further comprise at least one protic solvent.

In another embodiment of the present invention the oxygen content is controlled by using antioxidants or an inert gas such as nitrogen.

In a preferred embodiment the formulations are presented as a single vial presentation comprising 5-aza-2'-deoxycitidine in a concentration of 5 mg/ml.

The pharmaceutical compositions of the present invention are suitable for parenteral administration. These pharmaceutical compositions are then administered via intravenous infusion to treat patients suffering from myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and intermediate-1, intermediate2, and high-risk International Prognostic Scoring System groups.

In one embodiment of the present invention, the aprotic solvent is selected from the group consisting of 1-methyl-2-pyrrolidone, 1,3-dimethyl-2-imidazolidinone, dimethylacetamide, dimethyl sulfoxide, acetone, tetrahydrofuran, 1,4-dioxane, acetonitrile, dimethyl formamide, propylene carbonate, or mixtures thereof. Dimethylacetamide, dimethyl sulfoxide, or mixtures thereof are preferred. Dimethylacetamide is especially preferred.

In another embodiment of the present invention, the protic solvent is selected from the group consisting of alcohols, amides, or mixtures thereof. Alcohols, for example ethanol, are especially preferred.

In yet another embodiment of the present invention, the oxygen content is controlled by using antioxidants or inert gas such as nitrogen. This may be aided by, for example, purging the sealable container with a gas which is substantially oxygen-free, or substantially moisture free, or substantially oxygen and moisture free. Purging can be expected to reduce the oxygen level in the sealable container to a level of from about 0.5% to about 10%, typically about 5% or lower, depending on the efficiency of flushing and how quickly the container is sealed after flushing. The gas used for purging the sealable container may be any appropriate inert gas known to those in the art, the most commonly used gases being argon, helium or nitrogen, or mixtures thereof. However the most preferred inert gas is nitrogen.

In yet another embodiment of the present invention decitabine is not micronized. It has surprisingly been found that the micronization step is not necessary when preparing the compositions according to the present invention. Hence, these are more cost efficient and economical.

The invention is further illustrated by the following examples, which are not construed to be limiting the scope of the invention.

EXAMPLES

Example 1

The composition of the present invention contains decitabine in a concentration of 5 mg/mL in a solvent system comprising dimethylacetamide and ethanol in the ratio of 70:30. The details of the composition are shown in Table 1.

TABLE 1

Composition according to example 1 containing dimethylacetamide and ethanol in the ratio of 70:30

| Sr. No. | Ingredients | Quantity (mg/mL) |
|---|---|---|
| 1 | Decitabine | 5 mg |
| 2 | Dimethylacetamide | 0.7 mL |
| 3 | Ethanol | qs to 1 mL |
| 4 | Nitrogen* | qs |

*Nitrogen is used for purging in bulk solution and blanketing in vial headspace

The pharmaceutical composition according to example 1 was prepared by the following process:

A suitable quantity of dimethylacetamide was fed into a manufacturing vessel and subsequently the required quantity of alcohol was added. The two components were then mixed. Nitrogen was then purged into the solution obtained in the previous step until the oxygen content was below 7 mg/L, preferably below 3 mg/L. Decitabine was added and stirred in about 80% of the solution obtained in the previous step and dissolved. The volume was then made up to 100% with the solution obtained in step 2. The resulting Decitabine solution was then filtered through a suitable sterilizing grade filter and filled into vials. The vial headspace was then blanketed with nitrogen to achieve a headspace oxygen content of less than 10%, preferably less than 5%, more preferably less than 2%. Finally the vials were stoppered and sealed.

The stability profile of the formulation according example 1 was analysed and is presented in Table 2. The amount of Decitabine in the composition was measured before and after storage. The term "assay" as used in table 2 refers to the quantitative determination of decitabine via HPLC. Also, the impurity profile of the composition was analyzed before and after storage at various temperature and humidity conditions.

TABLE 2

Stability data of the composition according to example 1

| Stability Conditions | Assay (%) | Water by KF | Related Substances (% w/w) Total impurity |
|---|---|---|---|
| Initial | 102.8 | 0.42 | 0.15 |
| 40° C./75% RH (7 days) | 100.9 | 0.34 | 0.44 |
| Accelerated stability condition | 102.9 | 0.24 | 0.85 |

TABLE 2-continued

Stability data of the composition according to example 1

| Stability Conditions | Assay (%) | Water by KF | Related Substances (% w/w) Total impurity |
|---|---|---|---|
| 25° C./60% RH (3 M) Accelerated stability condition | 102.1 | 0.26 | 0.90 |
| 25° C./60% RH (6 M) Real time stability condition 2-8° C. (3 M) | 103.4 | 0.23 | 0.36 |
| Real time stability condition 2-8° C. (6 M) | 102.9 | 0.28 | 0.27 |

Example 2

The composition of the present invention contains Decitabine in a concentration of 5 mg/mL in a solvent system comprising dimethylacetamide and ethanol in the ratio of 60:40.

The details of the composition are given in table 3.

TABLE 3

Composition according to example 2 containing dimethylacetamide and ethanol in the ratio of 60:40

| Sr. No. | Ingredients | Quantity (mg/mL) |
|---|---|---|
| 1 | Decitabine | 5 mg |
| 2 | Dimethylacetamide | 0.6 mL |
| 3 | Ethanol | qs to 1 mL |
| 4 | Nitrogen* | qs |

*Nitrogen is used for purging in bulk solution and blanketing in vial headspace

The pharmaceutical composition according to example 2 was prepared by the following process:

A suitable quantity of dimethylacetamide was fed into a manufacturing vessel and subsequently the required quantity of alcohol was added. The two components were then mixed. Nitrogen was then purged into the solution obtained in the previous step until the oxygen content was below 7 mg/L, preferably below 3 mg/L. Decitabine was added and stirred in about 80% of the solution obtained in the previous step and dissolved. The volume was then made up to 100% with solution obtained in step 2. The drug solution was then filtered through a suitable sterilizing grade filter and filled into vials. The vial headspace was then blanketed with nitrogen to achieve a headspace oxygen content of less than 10%, preferably less than 5%, more preferably less than 2%. Finally the vials were stoppered and sealed.

The stability profile of the formulation according to example 2 was analyzed by subjecting the samples to various conditions and is presented in table 4. The amount of Decitabine in the composition was measured before and after storage. (The term "assay" as used in table 2 refers to the quantitative determination of decitabine via HPLC.) Also, the impurity profile of the formulation was analyzed before and after storage at various conditions.

TABLE 4

Stability Data of Representative Formulation (Example-2)

| Stability Conditions | Assay (%) | Water by KF | Related Substances (% w/w) Total impurity |
|---|---|---|---|
| Initial | 100.0 | 0.41 | 0.13 |
| 40° C./75% RH (7 days) | 100.2 | 0.43 | 0.49 |
| 40° C./75% RH (1 month) | 102.9 | 0.31 | 1.09 |
| Accelerated stability condition 25° C./60% RH (3 M) | 100.4 | 0.46 | 0.83 |
| Accelerated stability condition 25° C./60% RH (6 M) | 98.9 | 0.48 | 1.08 |
| Real time stability condition 2-8° C. (3 M) | 101.1 | 0.47 | 0.28 |
| Real time stability condition 2-8° C. (6 M) | 100.3 | 0.47 | 0.20 |

From the stability data provided in the tables above it is apparent that the pharmaceutical compositions according to the present invention are stable under various storage conditions (both real time and accelerated stability conditions).

Also, the impurity profile is better than that of the reference formulation, the commercially available lyophilized product Dacogen®, under accelerated storage conditions.

We claim:

1. A ready to use pharmaceutical composition comprising unmicronized 5-aza-2'-deoxycitidine, at least one protic solvent, and at least one aprotic solvent, wherein the composition is non-aqueous, the at least one protic solvent is ethanol, the at least one aprotic solvent is dimethylacetamide, and the protic solvent and the aprotic solvent are present in a ratio of 10:90 to 50:50 (protic:aprotic).

2. The composition according to claim 1, wherein the 5-aza-2'-deoxycitidine is present in a concentration of 5 mg/ml.

3. The composition according to claim 1, wherein the protic and aprotic solvents are present in a protic:aprotic ratio of 30:70 to 40:60.

4. The composition according to claim 1, wherein the composition is a solution of 5-aza-2'-deoxycitidine.

5. A method of treating a patient suffering from a myelodysplastic syndrome, the method comprising administering to the patient a composition according to claim 1.

6. A container comprising the composition according to claim 1.

7. A ready to use pharmaceutical composition comprising 5 mg/ml unmicronized 5-aza-2'-deoxycitidine and a non-aqueous solvent system comprising ethanol and dimethylacetamide in a ratio of 30:70 to 40:60 (ethanol:dimethylacetamide) by volume.

8. The composition according to claim 7, wherein the ethanol:dimethylacetamide ratio is 30:70 by volume.

9. A container comprising the composition according to claim 8.

10. The composition according to claim 7, wherein the ethanol:dimethylacetamide ratio is 40:60 by volume.

11. A container comprising the composition according to claim 10.

12. A method of preparing a pharmaceutical composition comprising unmicronized 5-aza-2'-deoxycitidine, the method comprising the steps of:

a) dissolving at least one protic solvent in a suitable quantity of at least one aprotic solvent, wherein the protic solvent is ethanol and the aprotic solvent is dimethylacetamide;
b) purging nitrogen into the solution obtained in step a) until the oxygen content is below 7 mg/L;
c) dissolving the 5-aza-2'-deoxycitidine in about 80% of a predetermined volume of the solution obtained in step b);
d) making the volume up to 100% with solution obtained in step b) to form a drug solution;
e) filtering the drug solution and filling it into vials;
f) blanketing the headspace of the vials with nitrogen to achieve a headspace oxygen content of less than 10%; and
g) stoppering and sealing the vials, wherein the protic solvent and the aprotic solvent are present in a ratio of 10:90 to 50:50 (protic:aprotic).

13. The method according to claim 12, wherein the oxygen content in step b) is below 3 mg/L.

14. The method according to claim 12, wherein the oxygen content in step f) is less than 5%.

15. The method according to claim 12, wherein the oxygen content in step f) is less than 2%.

\* \* \* \* \*